United States Patent [19]

Flynn

[11] Patent Number: 4,749,526

[45] Date of Patent: Jun. 7, 1988

[54] PROCESS FOR PREPARING FLUORALIPHATIC ETHER-CONTAINING CARBONYL FLUORIDE COMPOSITIONS

[75] Inventor: Richard M. Flynn, White Bear Lake, Minn.

[73] Assignee: Minnesota Mining and Manufacturing Co., St. Paul, Minn.

[21] Appl. No.: 906,816

[22] Filed: Sep. 12, 1986

[51] Int. Cl.$^4$ .............................................. C07C 51/29
[52] U.S. Cl. ................................ 260/544 F; 560/184; 544/175
[58] Field of Search .................... 260/544 F; 560/184; 568/615; 544/175

[56] References Cited

U.S. PATENT DOCUMENTS

| | | | |
|---|---|---|---|
| 3,114,778 | 12/1963 | Fritz et al. | 260/544 F |
| 3,250,806 | 5/1966 | Warnell | 560/184 |
| 3,250,808 | 5/1966 | Moore et al. | 260/535 |
| 3,311,658 | 3/1967 | Warnell | 260/544 |
| 3,527,742 | 9/1970 | Pittman et al. | 560/184 |
| 3,699,156 | 10/1972 | Holland et al. | 260/486 H |
| 4,035,388 | 12/1975 | Martini | 260/340 |
| 4,118,421 | 10/1978 | Martini | 260/544 |

FOREIGN PATENT DOCUMENTS

| | | | |
|---|---|---|---|
| 976136 | 12/1962 | United Kingdom | 568/615 |
| 1529514 | 10/1976 | United Kingdom | 260/544 R |

OTHER PUBLICATIONS (Translation only) N. D. Zelinskii Institute of Organic Chemistry, Academy of Sciences of the USSR, Moscow.
Vilenchik et al., *Izv. Akad. Nauk. SSSR, Ser. Khim.*, (1983), pp. 1891–1893.

*Primary Examiner*—James H. Reamer
*Attorney, Agent, or Firm*—D. M. Sell; J. A. Smith; C. Truesdale

[57] ABSTRACT

Fluoroaliphatic ether-containing carbonyl fluoride compounds are prepared by reacting a fluorinated carbonyl compound with hexafluoropropylene oxide in the presence of at least one catalyst selected from potassium iodide, potassium bromide, cesium iodide, cesium bromide, rubidium iodide, and rubidium bromide.

17 Claims, No Drawings

PROCESS FOR PREPARING FLUORALIPHATIC ETHER-CONTAINING CARBONYL FLUORIDE COMPOSITIONS

This invention relates to a process for preparing fluoroaliphatic ether-containing carbonyl fluoride compositions.

The preparation of perfluoroalkoxypropionic acid fluorides by reaction of hexafluoropropylene oxide,

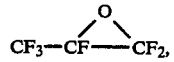

with perfluorocarboxylic acid fluorides in the presence of various catalysts is known. U.S. Pat. No. 3,250,808 (Moore et al.) discloses the reaction of hexafluoropropylene oxide with itself, fluoroalkanoic acid fluorides, or fluoroalkanones using various catalyst systems. The catalysts employed are activated charcoal, ionizing radiation, monovalent metal fluorides, particularly alkali metal fluorides, quaternary ammonium fluorides and alkali metal perfluoroalkoxides. The metal fluorides may be mixed with other alkali metal halides, e.g. lithium chloride/cesium fluoride, lithium chloride/potassium fluoride, and lithium bromide/potassium fluoride. U.S. Pat. No. 3,311,658 (Warnell) discloses the use of alkali metal fluorides, quaternary ammonium fluorides, silver fluorides, and alkali metal perfluoroalkoxides as catalysts. British Pat. No. 1,529,514 (duPont) discloses the use of sulfonium halides and complexes thereof as catalysts for the reaction of hexafluoropropylene oxide with fluorinated carbonyl compounds. U.S. Pat. No. 4,118,421 (Martini) discloses N,N,N',N'-tetrasubstituted difluorodiaminomethanes and U.S. Pat. No. 4,035,388 (Martini) discloses tris(dialkylamino)difluorophosphoranes as catalysts for the reaction of hexafluoropropylene oxide with perfluorocarboxylic acid fluorides and perfluorocarbonyl compounds, respectively. All of these catalysts serve to promote the formation of the perfluorinated alkoxide ion which is the species which undergoes reaction with the hexafluoropropylene oxide. It has also been reported [Izv. Akad. Nauk SSSR, Ser. Khim. 1891 (1983)] that the potassium halide salts potassium fluoride, potassium chloride, potassium bromide, and potassium iodide catalyze the oligomerization of hexafluoropropylene oxide, the use of the potassium fluoride resulting in the formation of hexafluoropropylene oxide oligomers up to the hexamer and the use of the potassium iodide resulting in the formation of mainly dimer and trimer.

This invention provides a process for preparing fluoroaliphatic ether-containing carbonyl fluoride compositions comprising reacting hexafluoropropylene oxide,

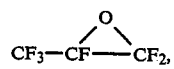

with a fluorinated carbonyl compound selected from fluorinated ketone and fluorinated acyl fluorides in the presence of at least one catalyst selected from potassium iodide, potassium bromide, cesium iodide, cesium bromide, rubidium iodide, and rubidium bromide.

Suitable reactive fluorinated carbonyl compounds useful in the process of the invention include those which can be represented by the general formula

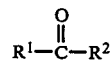   I where $R^1$ and $R^2$ are independently: F; fluoroalkyl groups, $R_f$, which are substantially perfluorinated and can be linear, branched or cyclic, and which can contain H, Cl or Br atoms and can contain catenary oxygen and/or trivalent nitrogen hetero atoms bonded only to carbon atoms of the skeletal chain, such hetero atoms providing stable linkages between fluorocarbon portions of the chain; fluorosulfonyl substituted perfluoroalkyl groups; fluorocarbonyl groups; fluorocarbonyl substituted perfluoroalkyl groups; alkoxycarbonyl substituted perfluoroalkyl groups; or $R^1$ and $R^2$ together with the $$\overset{O}{\underset{\|}{-C-}}$$

group can form a 4- to 7- membered ring; each of $R^1$ and $R^2$ having no more than 20 carbon atoms.

A subclass of the fluorinated carbonyl compounds useful in the process of this invention can be represented by the formula

   II where X is H, F, Cl, Br,

where R is a lower alkyl group having 1 to 8 carbon atoms, $FSO_2$—, or

and $R_f$ is a perfluoroalkylene group, having 1 to 20 carbon atoms, which is substantially perfluorinated and can be linear, branched or cyclic, and which can contain one or more H, Cl or Br atoms, and can contain catenary oxygen and/or trivalent nitrogen hetero atoms bonded only to carbon atoms of the skeletal chain, such hetero atoms providing stable linkages between fluorocarbon portions of the chain.

Fluorinated carbonyl compounds which can be used in the process of the invention include $COF_2$, FCOCOF, $CF_3COF$, $C_2F_5COF$, n-$C_3F_7COF$, i-$C_3F_7COF$, $C_2F_5OCF_2COF$, $C_3F_7OC(CF_3)FCOF$, $C_3F_7O[C(CF_3)FCF_2O]_3C(CF_3)FCOF$, $C_2F_5OCF_2CF_2OCF_2COF$, $H(CF_2)_6COF$, $BrCF_2COF$, $ClCF_2COF$, $FSO_2(CF_2)_3COF$, $CF_3COCF_3$, $HCF_2COCF_2H$, $FOCCF_2CF_2COF$, $FOCCF_2CF_2COOCH_3$, $CF_3COCF_2OC(CF_3)FCOOCH_3$, $CH_3SO_2CF_2CF_2COCF_3$, $CF_3CFHCOF$, $C_3F_7OC(CF_2Cl)FCOF$, $C_7F_{15}COF$, $C_3F_7OC(CF_2Cl)FCF_2OC(CF_2Cl)FCOF$, $(C_2F_5)_2NCF_2CF_2COF$, $FOCC(CF_3)FOCF_2CF_2COOCH_3$, $FOCC(CF_3)FOCF_2CF_2COOC_2H_5$,

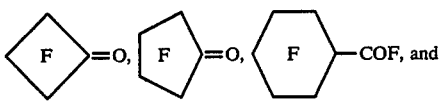=O, 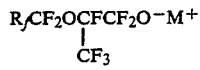—COF, and

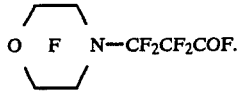 N—CF$_2$CF$_2$COF.

The fluoroaliphatic ether-containing carbonyl fluoride compositions produced by the process of this invention comprise mixtures of compounds represented by the formula $$R_fCF_2O(CFCF_2O)_pCFCOF$$
$$\phantom{R_fCF_2O(}|\phantom{CFCF_2O)_p}|$$
$$\phantom{R_fCF_2O(}CF_3\phantom{CF_2O)_p}CF_3$$

where $R_f$ is as defined above and p is zero or a number up to about 10 or higher.

Representative reaction schemes illustrative of the process of the invention are shown below. In each scheme $R_f$ is as defined above, M is K, Rb or Cs, X is bromide or iodide, and p is a number from 1 to about 10.

Scheme 1

Scheme 2

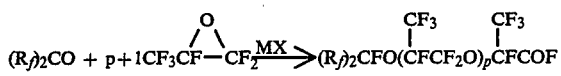

The process of this invention is preferably carried out in a polar organic solvent. Suitable solvents include aliphatic ethers such as diglyme, triglyme, and tetraglyme, with diglyme (diethylene glycol dimethyl ether) being generally more preferred, although the higher boiling point solvents, e.g., tetraglyme, are more preferred where recovery of low boiling point fluoroaliphatic ether-containing carbonyl fluoride compounds from the reaction product is required. Other solvents such as acetone or acetonitrile may also be employed. Reaction temperatures can vary widely, e.g., from about −80° to 100° C., preferably −30° to 60° C. Reaction time is generally from several minutes to about 50 hours depending on the scale of the reaction, with larger scale reactions requiring longer times. The reaction is generally carried out at atmospheric pressure, although higher pressure can be used, and requires no special equipment. To perform the reaction, the solvent and the fluorinated carbonyl compounds are charged to the reaction vessel and the catalyst is then added followed by addition of the hexafluoropropylene oxide, or the solvent and catalyst are charged to the reaction vessel and the fluorinated carbonyl compound is added and then the hexafluoropropylene oxide is added. Generally, processes for producing carbonyl fluoride compositions must be carried out under scrupulously anhydrous conditions, i.e., less than 100 ppm water, to prevent hydrolysis of the transitory intermediate perfluoroalkoxide, $$R_fCF_2OCFCF_2O^-M^+$$
$$\phantom{R_fCF_2OC}|$$
$$\phantom{R_fCF_2OC}CF_3$$

which would result in the formation of $$R_fCF_2OCFCOOH.$$
$$\phantom{R_fCF_2OC}|$$
$$\phantom{R_fCF_2OC}CF_3$$

Surprisingly, the process of the present invention need only be carried out under substantially anhydrous conditions, i.e., less than 2000 ppm, more preferably less than 1000 ppm water.

The preferred catalysts are potassium iodide and potassium bromide. Potassium chloride alone does not catalyze the reaction, although it will give a small yield of the desired products when a crown ether such as 18-crown-6 is employed as a co-catalyst.

The fluoroaliphatic ether-containing carbonyl fluoride compositions resulting from the reaction can be recovered from the reaction product mixture by phase separation followed by distillation.

The yields of the fluoroaliphatic ether-containing carbonyl fluoride composition from the reaction employing the catalysts of this invention are high, e.g., generally 50% or more based on the fluorinated carbonyl compound when the catalyst is potassium iodide or bromide, such yields frequently superior to those obtained with more commonly utilized catalysts such as cesium fluoride. The composition of the recovered fluoroaliphatic ether-containing carbonyl fluoride composition is substantially the same as that obtained by using cesium fluoride as the catalyst, although when potassium bromide is used as the catalyst there is a small amount of bromine-containing material in the final product.

In admixture with the fluoroaliphatic monoether compounds (Scheme 1, where p is 1), there are fluoroaliphatic polyether compounds which are formed by the addition of more units of hexafluoropropylene oxide, e.g., where p is 2 to 10 or higher. Under the appropriate conditions, e.g. when a higher molar ratio of hexafluoropropylene oxide to fluorinated carbonyl reactant is used, the polyether materials may become the major products.

The concentration of the catalyst used is, functionally stated, a catalytic amount, and this amount can be empirically determined. Generally that amount need not exceed about 12 mole percent based on the fluorinated carbonyl compound when potassium iodide is the catalyst. With potassium bromide, it is occasionally necessary to use somewhat larger amounts of catalyst ranging up to 100 mole percent based on the fluorinated carbonyl compound. The use of higher amounts of catalyst than that determined empirically is not detrimental to the reaction but offers no particular advantages.

The fluoroaliphatic ether-containing carbonyl fluorides produced by the process of this invention are useful intermediates for the preparation of many derivatives, e.g., carboxylic acids and their salts, esters, amides, alcohols, acrylates, vinyl ethers, polymers, etc., as described in U.S. Pat. Nos. 3,250,808 (Moore et al.) and 3,699,156 (Holland et al.) which are incorporated by reference for this purpose. These derivatives have utility for various applications, such as surfactants, lubricants, heat transfer and cooling fluids, hydraulic fluids and vapor phase heating.

To further illustrate this invention, the following nonlimiting examples are provided. In these examples, amounts are in weight percent unless otherwise indicated. All products had physical and analytical properties which were fully consistent with their structure and agreed with the data from products prepared by an alternate route. Gas chromatographic (GC) analysis of the reaction products, after conversion to the methyl esters, using a 3 meter OV101 column, gave baseline separation of the starting materials and the fluoroaliphatic ether products. Infrared (IR) spectral analysis of the products showed the characteristic carbonyl fluoride stretch at 5.22 microns. Fluorine nuclear magnetic resonance ($^{19}$F NMR) analysis was occasionally complicated by the presence of isomers and non-carbonyl-containing impurities present in the original starting acid fluorides, as well as some overlap in the 75-85 ppm range, but showed the characteristic -COF fluorine at +26 ppm downfield from the internal CFCl$_3$ standard. Mass spectral (MS) analysis was also carried out in some cases. Additional confirmation of the aliphatic ether-containing carbonyl fluoride products was obtained by conversion to the corresponding perfluorinated vinyl ether using standard procedures as described in U.S. Pat. No. 3,250,808 (Moore et al.) Yields were based on GC area percentages corrected for non-hexafluoropropylene oxide derived materials.

EXAMPLE 1

Potassium iodide (5.0 g, 0.03 mole) (Fisher, certified ACS), which had been vacuum dried, was added to 50 g dry (by distillation from sodium benzophenone ketyl) diglyme, (CH$_3$OC$_2$H$_4$)$_2$O, (Aldrich Chemical Co., 99%) contained in a 250 ml, 3-necked round bottom flask equipped with a Dry Ice-acetone condenser, an overhead stirrer and a gas inlet. To this stirred mixture was added, all at once, perfluorocyclohexane carbonyl fluoride

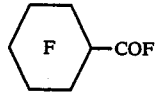

(100 g of 85% purity, 0.26 mole). After stirring for one hour at 0° C., hexafluoropropylene oxide (56 g of 80% purity, 0.27 mole) was added through the gas inlet over a period of 45 minutes. After stirring for two hours, the lower fluorochemical phase (143 g) was separated. Analysis of the fluorochemical phase by GC, IR, and $^{19}$F NMR showed that the phase contained 76% fluoroaliphatic ether-containing carbonyl fluoride products,

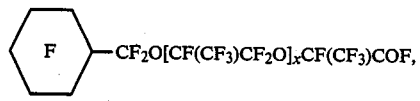

with the product distribution being x=0 (45%), x=1 (38%), and x≧2 (17%) for a yield of 57% based on perfluorocyclohexane carbonyl fluoride; 20% unreacted starting acid fluoride; and 4% hexafluoropropylene oxide oligomers, C$_3$F$_7$O[CF(CF$_3$)CF$_2$O]$_y$CF(CF$_3$)COF, where y is 0 to 2.

EXAMPLE 2

Fluoroaliphatic ether-containing carbonyl fluoride compounds were prepared as in Example 1, except the diglyme solvent was not distilled. Analysis of the fluorochemical phase by GC, IR, and $^{19}$F NMR showed that the phase contained 64% fluoroaliphatic ether-containing carbonyl fluoride compounds,

with the product distribution being x=0 (65%), x=1 (29%), and x≧2 (36%) for a yield of 50% based on the perfluorocyclohexane carbonyl fluoride; 34% unreacted starting acid fluoride; and 2% hexafluoropropylene oxide oligomers, C$_3$F$_7$O[CF(CF$_3$)CF$_2$O]$_y$CF(CF$_3$)COF, where y is 0 to 2.

COMPARATIVE EXAMPLE 1

Fluoroaliphatic ether-containing carbonyl fluoride compounds were prepared as in Example 1, except that the diglyme solvent was not distilled and tetrabutylammonium iodide (0.03 mole, 11.1 g) (Eastman Kodak Co.), described as a catalyst for reacting hexafluoropropylene epoxide and omega-iodoacid fluorides in U.S. Pat. No. 3,311,658 (warnell) was substituted for the potassium iodide. Analysis of the fluorochemical phase by GC, IR, and $^{19}$F NMR showed that the phase contained 26% fluoroaliphatic ether-containing carbonyl fluoride compounds,

with the product distribution being x=0 (85%), x=1 (15%), and x≧2 (trace) for a yield of 22% based on the perfluorocyclohexane carbonyl fluoride, 64% unreacted starting acid fluoride, 10% hexafluoropropylene oxide oligomers, C$_3$F$_7$O[CF(CF$_3$)CF$_2$O]$_y$CF(CF$_3$)COF, where y is 0 to 2.

EXAMPLE 3

Potassium iodide (3.07 g, 0.018 mole) and diglyme (42 g) were combined as in Example 1 and cooled to −20° C. Tetrafluorosuccinyl fluoride, FCOCF$_2$CF$_2$COF (40 g of 75% purity, 0.15 mole), was added and the mixture stirred for 45 minutes. Hexafluoropropylene oxide (50 g of 80% purity, 0.30 mole) was added over 45 minutes. The reaction mixture was separated. The lower fluorochemical phase contained: 35% FOC(CF$_2$)$_3$OCF(CF$_3$)COF and 49% FOCCF(CF$_3$)O(CF$_2$)$_4$OCF(CF$_3$)COF, a yield of 95% based on tetrafluorosuccinyl fluoride. The remainder (16%) of the fluorochemical phase was starting material and a small amount of hexafluoropropylene oxide oligomers.

EXAMPLE 4

Potassium iodide (1.7 g, 0.01 mole) and diglyme (50 g) were combined as in Example 1 and cooled to −20° C. Trifluoroacetyl fluoride, CF$_3$COF (10 g, 0.086 mole), was added as a gas over a period of about 10 minutes with stirring and the mixture was further stirred for 20 minutes. Hexafluoropropylene oxide (17.9 g of 80% purity, 0.086 mole) was added and the mixture stirred until reflux from the Dry Ice condenser had ceased. The fluorochemical product layer was separated and reacted with methanol-BF$_3$ at 0°–5° C. for 10 minutes to convert the volatile acyl fluorides to the corresponding methyl ester. The product contained about 100% fluoroaliphatic ether-containing methyl ester compounds, $C_2F_5O[CF(CF_3)CF_2O]_xCF(CF_3)CO_2CH_3$, with the product distribution being x=0 (49%), x=1 (45%) and x=2 (6%). Yield of the product was 56% based on $CF_3COF$. Trace amounts of hexafluoropropylene oxide oligomers were also formed.

EXAMPLE 5

Potassium iodide (4.5 g, 0.027 mole) and diglyme (60 g) were combined as in Example 1 and cooled to −20° C. Heptafluorobutyryl fluoride, $C_3F_7COF$ (70.9 g of 43% purity, 0.14 mole) was added and the mixture stirred. Hexafluoropropylene oxide (58.5 g of 80% purity, 0.28 mole) was added over 30 minutes. The reaction mixture was allowed to warm to about 25° C. over a five-hour period and the resulting product was found to contain 91% fluoroaliphatic ether-containing carbonyl fluoride compounds, $C_4F_9O[CF(CF_3)CF_2O]_xCF(CF_3)COF$, with the product distribution being x=0 (23%), x=1 (54%) and x=2 (23%), in a nearly quantitative yield based on $C_3F_7COF$. Nine percent of the fluorochemical product was hexafluoropropylene oxide oligomers.

EXAMPLE 6

Using the procedure of Example 1, potassium bromide (2.59 g, 0.022 mole), diglyme (100 g) and perfluoro(morpholinopropionyl) fluoride,

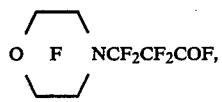

(100 g of 68% purity, 0.18 mole) were combined and stirred at 25° C. for one hour. The reaction mixture was cooled to 0° C. and hexafluoropropylene oxide (40 g of 80% purity, 0.19 mole) was added over a period of 30 minutes. After an additional period of about 4 hours of stirring, the reaction mixture was allowed to warm to about 25° C. over a 2-hour period and the phases were separated. The lower fluorochemical phase was analyzed and found to contain 52% fluoroaliphatic ether-containing carbonyl fluoride compounds,

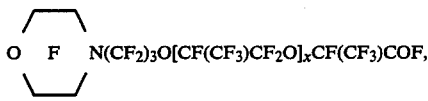

with the product distribution being x=0 (79%), x=1 (12%) and x=2 (9%) in a yield of 60% based on starting acyl fluoride. The remainder of the fluorochemical phase was starting material (38%) and hexafluoropropylene oxide oligomers (10%).

EXAMPLE 7

Using the procedure of Example 1, potassium iodide (2.55 g, 0.015 mole), diglyme (80 g) and perfluoro(diethylaminopropionyl) fluoride, $(C_2F_5)_2NCF_2CF_2COF$, (100 g of 51% purity, 0.129 mole) were combined and stirred at 0° C. for 45 minutes. Hexafluoropropylene oxide (28 g of 80% purity, 0.135 mole) was added and the mixture stirred for 4 hours and then slowly allowed to warm to about 25° C. over a 2-hour period. The resulting two-phase reaction mixture was separated and the lower fluorochemical phase analyzed and found to contain 59% fluoroaliphatic ether-containing carbonyl fluoride compounds, $(C_2F_5)_2N(CF_2)_3O[CF(CF_3)CF_2O]_xCF(CF_3)COF$, with the product distribution being x=0 (80%) and x=1 (20%), in a yield of 76% based on starting acyl fluoride. The remainder of the fluorochemical product was starting material and hexafluoropropylene oxide oligomers.

EXAMPLE 8

Potassium iodide (1.2 g, 0.007 mole) and diglyme (50 g) were combined as in Example 1 and cooled to −20° C. An extra condenser was placed on top of the first Dry Ice condenser and both were filled with Dry Ice-diethyl ether. Carbonyl fluoride, $COF_2$ (5.0 g, 0.076 mole) was added as a gas. Hexafluoropropylene oxide (25.1 g, 0.15 mole) was added over a fifteen minute period. The resulting mixture was stirred for two hours and the lower fluorochemical phase was then separated. For ease of analysis due to the volatility of the acyl fluoride, the product was converted to the methyl ester as in Example 4. GC-MS and $^{19}F$ NMR analysis of the reaction mixture showed the expected fluoroaliphatic ether-containing methyl ester compounds, $CF_3O[CF(CF_3)CF_2O]_xCF(CF_3)CO_2CH_3$, where x was 1 to 5, and an equal amount of hexafluoropropylene oxide oligomers.

EXAMPLE 9

Potassium iodide (1.20 g, 0.007 mole) and diglyme (50 g) were combined as in Example 1 and cooled to −20° C. Hexafluoroacetone (8.0 g, 0.048 mole) was condensed into the mixture and the suspension stirred for 25 minutes. Hexafluoropropylene oxide (20.0 g of 80% purity, 0.096 mole) was added over a period of 20 minutes and the resulting mixture stirred for two hours while slowly warming to about 25° C. The lower fluorochemical phase was separated to give 21.7 g of a mixture of fluoroaliphatic ether-containing carbonyl fluoride compounds, $(CF_3)_2CFO[CF(CF_3)CF_2O]_xCF(CF_3)COF$, where x=0 to 3 and hexafluoropropylene oxide oligomers in a 4:1 mole ratio.

EXAMPLE 10

Diglyme (92.5 kg) (Ansul E-141, Ansul Co.; water content 640 ppm) was charged into a 189 L refrigerated stainless steel reactor followed by the addition of potassium iodide (3.9 kg, 23.5 mole) (Mallinckrodt). The batch was cooled to −12° C. and $C_3F_7COF$ (77 kg of 51% purity, 181 mole) was added rapidly. The mixture was agitated for two hours at −12° C. Hexafluoropropylene oxide (77 kg, 464.9 mole) was subsequently added such that the temperature of the reaction did not exceed −12° C. After the addition of the hexafluoropropylene oxide was complete, the reactor was held for one hour at −18° to −12° C. The batch was then heated for 1 hour to 52° C. to remove the lower boiling impurities. After cooling to 21° C. over a 2 hour period, the bottom fluorochemical phase was separated to give 118 kg (80%) fluoroaliphatic ether-containing carbonyl fluoride compounds, $C_4F_9O[CF(CF_3)CF_2O]_xCF(CF_3)COF$, with the product distribution being x=0 (20%), x=1 (65%) and x=2 (15%), and 20% hexafluoropropylene oxide oligomers, C$_3$F$_7$O[CF(CF$_3$)CF$_2$O]$_x$CF(CF$_3$)COF, with the product distribution being x=0 (40%), x=1 (50%) and x=2 (10%). The mole percent yield of fluoroaliphatic ether-containing carbonyl fluoride compounds based on C$_3$F$_7$COF was 90% and based on hexafluoropropylene oxide was 82%.

EXAMPLE 11

Potassium iodide (7.1 g, 0.043 mole) and diglyme (94g) were combined as in Example 1. 4-(Fluorosulfonyl)hexafluorobutyryl fluoride, FO$_2$S(CF$_2$)$_3$COF, (173 g of 58% purity, 0.358 mole) was added at 25° C. and the contents stirred for 30 minutes and then cooled to 0° C. Hexafluoropropylene oxide (151 g, 0.910 mole) was added over four hours with the bulk (120 g) added within the first hour. After the reaction was complete, the phases were separated and the lower fluorochemical phase (290 g) was analyzed and found to contain 64% fluoroaliphatic ether-containing carbonyl fluoride compounds, FO$_2$S(CF$_2$)$_4$O[CF(CF$_3$)CF$_2$O]$_x$CF(CF$_3$)COF, with the product distribution being x=0 (17%), x=1 (72%) and x=2 (11%), in a yield of 89% based on starting acid fluoride. The remainder of the fluorochemical phase (36%) was starting material.

EXAMPLE 12

Fluoroaliphatic ether-containing carbonyl fluoride compounds were prepared as in Example 1, except the diglyme solvent was not distilled and rubidium bromide (0.03 mole, 4.96 g) (Aldrich Chemical Co.) was substituted for the potassium iodide. Analysis of the fluorochemical phase by GC, IR, and $^{19}$F NMR showed that the phase contained 37% fluoroaliphatic ether-containing carbonyl fluoride compounds,

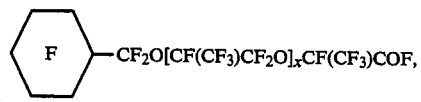

with the product distribution being x=0 (86%), x=1 (14%), and x≧2 (trace) for a yield of 33% based on perfluorocyclohexane carbonyl fluoride, 56% unreacted starting acid fluoride, and 7% hexafluoropropylene oxide oligomers, C$_3$F$_7$O[CF(CF$_3$)CF$_2$O]$_y$CF(CF$_3$)COF, where y is 0 to 2.

EXAMPLE 13

Fluoroaliphatic ether-containing carbonyl fluoride compounds were prepared as in Example 1, except the diglyme solvent was not distilled and rubidium iodide (0.03 moles, 6.37 g) (Alfa Inorganics Inc.) was substituted for the potassium iodide. Analysis of the fluorochemical phase by GC, IR, and $^{19}$F NMR showed that the phase contained 42% fluoroaliphatic ether-containing carbonyl fluoride compounds,

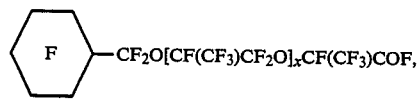

with the product distribution being x=0 (83%), x=1 (14%), and x≧2 (3%) for a yield of 36% based on perfluorocyclohexane carbonyl fluoride; 50% unreacted starting acid fluoride; and 8% hexafluoropropylene oxide oligomers, C$_3$F$_7$O[CF(CF$_3$)CF$_2$O]$_y$CF(CF$_3$)COF, where y is 0 to 2.

EXAMPLE 14

Fluoroaliphatic ether-containing carbonyl fluoride compounds were prepared as in Example 1, except the diglyme solvent was not distilled and cesium bromide (0.03 moles, 6.38 g) (Aldrich Chemical Co.) was substituted for the potassium iodide. Analysis of the fluorochemical phase by GC, IR, and $^{19}$F NMR showed that the phase contained 3% fluoroaliphatic ether-containing carbonyl compounds,

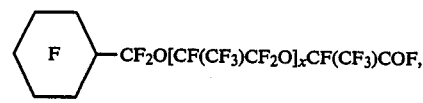

with the product distribution being x=0 (99%) and x=1 (trace) for a yield of 2.7% based on the perfluorocyclohexane carbonyl fluoride; 86% unreacted starting acid fluoride; and 11% hexafluoropropylene oxide oligomers, C$_3$F$_7$O[CF(CF$_3$)CF$_2$O]$_y$CF(CF$_3$)COF, where y is 0 to 2.

EXAMPLE 15

Fluoroaliphatic ether-containing carbonyl fluoride compounds were prepared as in Example 1, except the diglyme solvent was not distilled and cesium iodide (0.03 moles, 7.8 g) (Aldrich Chemical Co.) was substituted for the potassium iodide. Analysis of the fluorochemical phase by GC, IR, and $^{19}$F NMR showed that the phase contained 7% fluoroaliphatic ether compounds,

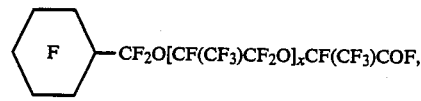

with the product distribution being x=0 (>99%) and x=1 (trace) for a yield of 6% based on the perfluorocyclohexane carbonyl fluoride; 78% unreacted starting acid fluoride; and 15% hexafluoropropylene oxide oligomers, C$_3$F$_7$O[CF(CF$_3$)CF$_2$O]$_y$CF(CF$_3$)COF, where y is 0 to 2.

The various modifications and alterations of this invention will be apparent to those skilled in the art without departing from the scope and spirit of this invention and this invention should not be restricted to that set forth herein for illustrative purposes.

What is claimed is:

1. A process for preparing fluoroaliphatic ether-containing carbonyl fluoride compounds comprising reacting hexafluoropropylene oxide with a fluorinated carbonyl compound selected from fluorinated ketone and fluorinated acyl fluorides in the presence of at least one catalyst selected from potassium iodide, potassium bromide, rubidium iodide, and rubidium bromide.

2. The process of claim 1 wherein said reaction is conducted in a polar organic solvent.

3. The process of claim 1 wherein said process is carried out under substantially anhydrous conditions.

4. The process of claim 1 wherein said reaction is conducted at a temperature of about −80° C. to 100° C.

5. The process of claim 1 wherein said process further comprises recovering said fluoroaliphatic ether-containing carbonyl fluoride compounds by phase separatio followed by distillation.

6. The process of claim 1 wherein said fluorinated carbonyl compound is represented by the formula

    I where $R^1$ and $R^2$ are independently F; fluoroalkyl groups, $R_f$, which are substantially perfluorinated and can be linear, branched or cyclic, and which can contain H, Cl or Br atoms and can contain catenary oxygen and/or trivalent nitrogen hetero atoms bonded only to carbon atoms of the skeletal chain, such hetero atoms providing stable linkages between fluorocarbon portions of the chain; fluorosulfonyl substituted perfluoroalkyl groups; fluorocarbonyl groups; fluorocarbonyl substituted perfluoroalkyl groups; alkoxycarbonyl substituted perfluoroalkyl groups; or the $R^1$ and $R^2$ together with the

group can form a 4- to 7-membered ring; each of $R^1$ and $R^2$ having no more than 20 carbon atoms.

7. The process of claim 1 wherein said fluorinated carbonyl compound is represented by the formula

    II where X is H, F, Cl, Br,

where R is lower alkyl, $FSO_2-$, or

;

and $R_f$ is a fluoroalkylene group, having 1 to 20 carbon atoms, which is substantially perfluorinated and can be linear, branched or cyclic, and which can contain one or more H, Cl, or Br atoms, and can contain catenary oxygen and/or trivalent nitrogen hetero atoms bonded only to carbon atoms of the skeletal chain, such hetero atoms providing stable linkages between fluorocarbon portions of the chain.

8. The process of claim 1 wherein said fluorinated carbonyl compound is $COF_2$, $FCOCOF$, $CF_3COF$, $C_2F_5COF$, $n\text{-}C_3F_7COF$, $i\text{-}C_3F_7COF$, $C_2F_5OCF_2COF$, $C_3F_7OC(CF_3)FCOF$, $C_3F_7O[C(CF_3)FCF_2O]_3C(CF_3)FCOF$, $C_2F_5OCF_2CF_2OCF_2COF$, $H(CF_2)_6COF$, $BrCF_2COF$, $ClCF_2COF$, $FSO_2(CF_2)_3COF$, $CF_3COCF_3$, $HCF_2COCF_2H$, $FOCCF_2CF_2COF$, $FOCCF_2CF_2COOCH_3$, $C_7F_{15}COF$, $CF_3COCF_2OC(CF_3)FCOOCH_3$, $CH_3SO_2CF_2CF_2COCF_3$, $CF_3CFHCOF$, $C_3F_7OC(CF_2Cl)FCOF$, $C_3F_7OC(CF_2Cl)FCF_2OC(CF_2Cl)FCOF$, $(C_2F_5)_2NCF_2CF_2COF$, $FOCC(CF_3)FOCF_2CF_2COOCH_3$, $FOCC(CF_3)FOCF_2CF_2COOC_2H_5$,

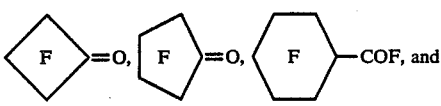

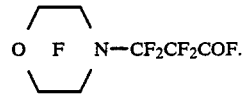

9. The proccess of claim 1 wherein said catalyst is potassium iodide or potassium bromide.

10. The process of claim 1 wherein said fluorinated carbonyl compound is perfluorocyclohexane carbonyl fluoride and said catalyst is potassium iodide.

11. The process of claim 1 wherein said fluorinated carbonyl compound is tetrafluorosuccinyl fluoride and said catalyst is potassium iodide.

12. The process of claim 1 wherein said fluorinated carbonyl compound is trifluoroacetyl fluoride and said catalyst is potassium iodide.

13. The process of claim 1 wherein said fluorinated carbonyl compound is carbonyl fluoride and said catalyst is potassium iodide.

14. The process of claim 1 wherein said fluorinated carbonyl compound is hexafluoroacetone and said catalyst is potassium iodide.

15. The process of claim 1 wherein said fluorinated carbonyl compound is heptafluorobutyryl fluoride and said catalyst is potassium iodide.

16. The process of claim 1 wherein said fluorinated carbonyl compound is 4-(fluorosulfonyl) hexafluorobutyryl fluoride and said catalyst is potassium iodide.

17. The process of claim 1 wherein said fluorinated carbonyl compound is pentadecafluorooctanyl fluoride and said catalyst is potassium iodide.

* * * * *

UNITED STATES PATENT AND TRADEMARK OFFICE
CERTIFICATE OF CORRECTION

PATENT NO. : 4,749,526
DATED : JUNE 7, 1988
INVENTOR(S) : RICHARD M. FLYNN

It is certified that error appears in the above-identified patent and that said Letters Patent is hereby corrected as shown below:

Col. 6, line 30, "warnell" should be -- Warnell -- .

Col. 6, line 56, "FOC(CF$_2$)$_3$OCF(CF3)-" should be -- FOC(CF$_2$)$_3$OCF(CF$_3$)- -- .

Col. 12, line 20, "-COF, and" should be -- -COF, or -- .

Signed and Sealed this

Eleventh Day of July, 1989

Attest:

DONALD J. QUIGG

Attesting Officer

Commissioner of Patents and Trademarks